(12) United States Patent
Hall

(10) Patent No.: US 12,396,877 B2
(45) Date of Patent: Aug. 26, 2025

(54) CUSTOMIZABLE FITTED APPARATUS

(71) Applicant: Diana Hall, Pueblo, CO (US)

(72) Inventor: Diana Hall, Pueblo, CO (US)

(*) Notice: Subject to any disclaimer, the term of this patent is extended or adjusted under 35 U.S.C. 154(b) by 272 days.

(21) Appl. No.: 17/934,052

(22) Filed: Sep. 21, 2022

(65) Prior Publication Data
US 2023/0014237 A1    Jan. 19, 2023

Related U.S. Application Data

(63) Continuation of application No. 16/677,434, filed on Nov. 7, 2019, now abandoned, which is a
(Continued)

(51) Int. Cl.
*A61F 5/00* (2006.01)
*A61F 5/01* (2006.01)
*A61F 5/058* (2006.01)

(52) U.S. Cl.
CPC ........ *A61F 5/05858* (2013.01); *A61F 5/0104* (2013.01); *A61F 5/0585* (2013.01)

(58) Field of Classification Search
CPC ........ A61F 5/0111; A61F 2/38; A61F 5/0102; A61F 2/30756; A61F 2/30942; A61F 7/034; A61F 5/0118; A61F 5/01; A61F 2007/0098; A61F 2007/0268; A61F 5/0123; A61F 2/80; A61F 5/0127; A61F 2210/0085; A61F 5/0125; A61F 2210/0004; A61F 2220/0008; A61F 2220/005; A61F 2/7812; A61F 5/012; A61F 5/05866; A61F 2002/7635; A61F 5/0195; A61F 2220/0075; A61F 2220/0016; A61F 2220/0066;
(Continued)

(56) References Cited

U.S. PATENT DOCUMENTS 101,743 A    4/1870  King
2,761,443 A  9/1956  Parker
(Continued)

FOREIGN PATENT DOCUMENTS

WO    WO-2010099130 A1    9/2010

OTHER PUBLICATIONS

Office Action dated Nov. 14, 2018 for U.S. Appl. No. 14/852,516.
(Continued)

*Primary Examiner* — Kim M Lewis
(74) *Attorney, Agent, or Firm* — Plumsea Law Group, LLC

(57) ABSTRACT

A customizable fitted device for immobilizing injuries and a method for constructing the fitted device is provided. The fitted device can be used to stabilize an arm, wrist, hand, leg, knee, ankle, foot or other body parts through custom formation. The device can be formed by a sidewall having one or more sidewall sections that can be secured together using retaining clips positioned within retaining clip slots on the device. The device can further include one or more openings defined in the sidewall of each device section while maintaining rigidity in the sidewall. The device can be constructed by of creating a 3D image scan of the particular body part on which the device will be applied, creating a design of the device to precisely match the contours of the 3D image scan, and using a 3D printer to construct the device according to the design.

20 Claims, 11 Drawing Sheets

Related U.S. Application Data continuation of application No. 14/852,516, filed on Sep. 12, 2015, now abandoned.

(60) Provisional application No. 62/162,743, filed on May 17, 2015, provisional application No. 62/050,067, filed on Sep. 12, 2014.

(58) Field of Classification Search
CPC ........ A61F 2/013; A61F 2/014; A61F 2/2409; A61F 2/2415; A61F 2/2418; A61F 2/2427; A61F 2/2436; A61F 2/2439; A61F 2/76; A61F 2002/061; A61F 2002/068; A61F 2002/30583; A61F 2002/30672; A61F 2005/0172; A61F 2230/0054; A61F 2230/0078; A61F 2230/008; A61F 2250/0003; A61F 2250/0021; A61F 2250/0059; A61F 2/0811; A61F 2/30; A61F 2/78; A61F 2/54; A61F 2/7843; A61F 2002/5083; A61F 2002/2835; A61F 2005/0165; A61F 2002/0858; A61F 5/0106; A61F 2/5046; A61F 2002/3093; A61F 13/04; A61F 2/0805; A61F 2/3877; A61F 2002/0852; A61F 2002/0882; A61F 2002/3895; A61F 2005/0179; A61F 2240/008; A61F 2/74; A61F 2002/704; A61F 5/028; A61F 5/05816; A61F 5/0585; A61F 2230/0013; A61F 5/058; A61F 5/32; A61F 2/07; A61F 2007/0062; A61F 5/055; A61F 2/60; A61F 2/82; A61F 2002/0086; A61F 2002/5053; A61F 2230/0082; A61F 2002/30062; A61F 2002/5027; A61F 5/013; A61F 2/70; A61F 2/90; A61F 2250/001; A61F 5/05; A61F 2/2846; A61F 2/389; A61F 2002/5026; A61F 2002/5055; A61F 2002/7655; A61F 2005/0134; A61F 2220/0025; A61F 7/0085; A61F 13/00063; A61F 2/28; A61F 2007/0292; A61F 5/019; A61F 5/026; A61F 5/566; A61F 7/03; A61F 2/4455; A61F 2/5044; A61F 2002/30677; A61F 2002/3096; A61F 2002/5052; A61F 2005/0137; A61F 2005/0167; A61F 2230/001; A61F 2310/00179; A61F 5/05875; A61F 13/05; A61F 13/15804; A61F 2/3094; A61F 2002/0829; A61F 2002/0888; A61F 2002/7625; A61F 5/14; A61F 13/023; A61F 2002/3069; A61F 5/10; A61F 13/00085; A61F 13/15; A61F 13/15772; A61F 2/0077; A61F 2/064; A61F 2/582; A61F 2/72; A61F 2002/2839; A61F 2002/285; A61F 2002/3068; A61F 2002/30971; A61F 2002/5018; A61F 2002/764; A61F 2002/785; A61F 2002/7862; A61F 2250/0068; A61F 5/56; A61F 11/00; A61F 13/00; A61F 13/01021; A61F 13/0279; A61F 13/4902; A61F 2/30965; A61F 2/44; A61F 2/741; A61F 2002/30065; A61F 2002/30387; A61F 2002/30841; A61F 2002/701; A61F 2007/0056; A61F 2013/00357; A61F 2013/00536; A61F 2210/0071; A61F 13/84; A61F 2/04; A61F 2/32; A61F 2/34; A61F 2002/2817; A61F 2002/30133; A61F 2002/5007; A61F 2002/502; A61F 2002/7837; A61F 2002/7875; A61F 2005/0174; A61F 5/05841; A61F 5/34; A61F 11/14; A61F 13/02; A61F 2/40; A61F 2002/2825; A61F 2002/30578; A61F 2002/30588; A61F 2002/30593; A61F 2002/30604; A61F 2002/30892; A61F 2002/30963; A61F 2002/4619; A61F 2002/5003; A61F 2002/7881; A61F 2002/802; A61F 2005/0176; A61F 2005/0197; A61F 2007/0238; A61F 2240/005; A61F 2310/00017; A61F 2310/00023; A61F 2310/00029; A61F 2310/00365; A61F 5/3753; A61F 7/00; A61F 7/10; A61F 13/046; A61F 13/08; A61F 13/496; A61F 13/58; A61F 2/02; A61F 2/581; A61F 2/64; A61F 2002/3007; A61F 2002/5001; A61F 2002/5016; A61F 2002/509; A61F 2002/7665; A61F 2002/7675; A61F 2002/7831; A61F 2007/0008; A61F 2007/0009; A61F 2007/0018; A61F 2007/0042; A61F 2007/006; A61F 5/0104; A61F 5/24; A61F 7/08; A61F 7/106; A61F 13/493; A61F 13/53; A61F 2/3859; A61F 2/46; A61F 2/4603; A61F 2/4644; A61F 2002/30059; A61F 2002/30064; A61F 2002/30072; A61F 2002/30433; A61F 2002/30563; A61F 2002/4627; A61F 2002/4645; A61F 2005/0181; A61F 2007/0001; A61F 2220/0041; A61F 2230/00; A61F 2310/00592; A61F 2310/00958; A61F 2310/0097; A61F 5/0076; A61F 5/0109; A61F 13/041; A61F 13/49; A61F 13/49011; A61F 2/0063; A61F 2/91; A61F 2/915; A61F 2002/30462; A61F 2002/30522; A61F 2002/30952; A61F 2002/5049; A61F 2002/5056; A61F 2002/608; A61F 2005/0158; A61F 2013/530481; A61F 2013/530547; A61F 2250/0067; A61F 5/0083; A61F 5/0086; A61F 5/022; A61F 13/06; A61F 13/539; A61F 13/5622; A61F 2/30734; A61F 2/30749; A61F 2/30771; A61F 2/30907; A61F 2/4609; A61F 2/6607; A61F 2002/30011; A61F 2002/3008; A61F 2002/30092; A61F 2002/30169; A61F 2002/30189; A61F 2002/3023; A61F 2002/30261; A61F 2002/30326; A61F 2002/30331; A61F 2002/30405; A61F 2002/30426; A61F 2002/30448; A61F 2002/30449; A61F 2002/30451; A61F 2002/30471; A61F 2002/30474; A61F 2002/305; A61F 2002/30507; A61F 2002/30538; A61F 2002/3055; A61F 2002/30556; A61F 2002/30579; A61F 2002/30599; A61F 2002/30616; A61F 2002/30617; A61F 2002/30736; A61F 2002/3082; A61F 2002/30828; A61F 2002/3085; A61F 2002/30879; A61F 2002/30891; A61F 2002/30904; A61F 2002/3092; A61F 2002/30985; A61F 2002/3412; A61F 2002/3429; A61F 2002/3441; A61F 2002/3448; A61F 2002/348; A61F 2002/3487; A61F
2002/4615; A61F 2002/4683; A61F
2002/5023; A61F 2002/607; A61F
2002/6621; A61F 2002/6642; A61F
2002/7818; A61F 2002/91541; A61F
2005/412; A61F 2005/417

See application file for complete search history.

(56) References Cited

U.S. PATENT DOCUMENTS

| | | | | |
|---|---|---|---|---|
| 4,436,088 | A * | 3/1984 | Finnieston | A61F 5/05858 602/20 |
| 5,836,902 | A | 11/1998 | Gray | |
| 10,343,309 | B2 * | 7/2019 | Cuypers | A61F 5/37 |
| 10,940,031 | B2 * | 3/2021 | Joseph | A61F 5/055 |
| 11,648,142 | B2 * | 5/2023 | L? | B33Y 80/00 703/2 |
| 11,963,889 | B2 * | 4/2024 | Parr | A61B 17/8061 |
| 2012/0004587 | A1 | 1/2012 | Nickel | |

OTHER PUBLICATIONS

Office Action dated Aug. 7, 2019 for U.S. Appl. No. 14/852,516.
Paterson et al., Computer-aided design to support fabrication of wrist splints using 3D printing: a feasibility study,2014, Hand Therapy, vol. 19(4), pp. 102-113. (Year: 2014).
First publishing date for Paterson et al. reference (Year: 2014).
Non-Final Office Action dated Mar. 28, 2022 for U.S. Appl. No. 16/677,434.

* cited by examiner

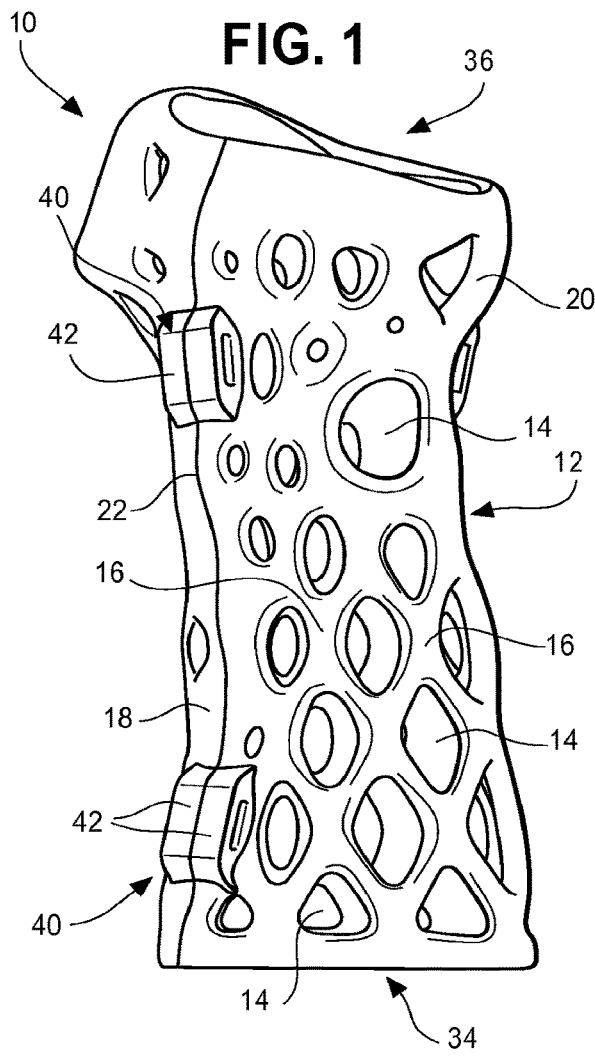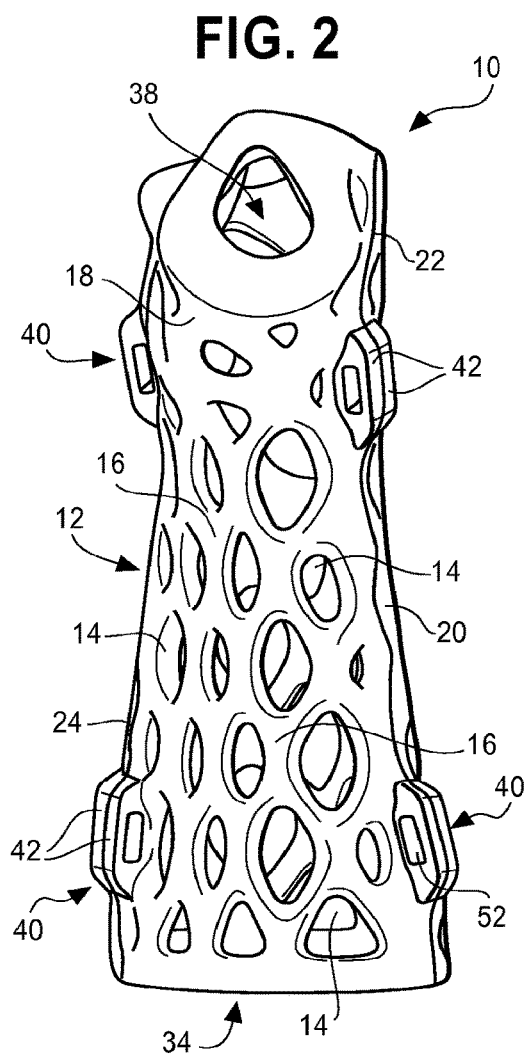

CUSTOMIZABLE FITTED APPARATUS

CROSS-REFERENCE TO RELATED APPLICATIONS

This application claims priority to currently pending U.S. patent application Ser. No. 16/677,434, filed on Nov. 7, 2019 to Diana Hall, entitled "Customizable Fitted Apparatus"; which in turn claimed priority to U.S. patent application Ser. No. 14/852,516 filed on Sep. 12, 2015 to Diana Hall, entitled "Customizable Fitted Apparatus"; which in turn claimed priority to U.S. patent application Ser. No. 62/162,743 filed on May 17, 2015 to Diana Hall, entitled "Amphibian Skin 3D Printed Clips and Cable Tie Slots"; and which also claimed priority to U.S. patent application Ser. No. 62/050,067, filed on Sep. 12, 2014 to Diana Hall, entitled "Amphibian Skin Custom-fit Exoskeleton Support Devices." The entire disclosures of each of these priority applications is hereby incorporated by reference.

BACKGROUND

1. Field of the Disclosure

The present invention relates to devices, such as casts, splints, braces, and similar devices for immobilizing and stabilizing various portions of a user's body, including arms, elbows, wrists, hands, legs, knees, ankles, feet and other structures. Such devices are also used in veterinary applications and other various alternative uses.

2. Description of Related Art

When a user's body portion needs stabilization, a cast, brace or similar device is commonly applied to immobilize the particular location of the identified body part. The cast or splint is commonly applied to an arm, leg, or joint, such as a knee, ankle, elbow or wrist. One common cast is a molded plaster or fiberglass cast formed around the location of the body part. A layer of padding, such as a cotton wrap, is applied around the body portion targeted and the plaster or fiberglass cast component is then applied and molded to conform to the patient's body. The cast is a single-use and non-removable device. While this style of casts is generally effective at immobilizing the targeted body portion and is generally inexpensive to produce, it has several limitations. One main limitation is that the cast is not removable. Thus, in order to clean the targeted body portion or subsequently examine the targeted body portion, the cast must be removed and a new cast applied. Another limitation is that this type of cast is non-breathable and non-waterproof. This can lead to skin irritation and other issues as well as damage to the cast when the patient encounters wet conditions.

Accordingly, a need exists for a moldable cast or similar device that is effective at immobilizing a particular body part while being removable, reusable, lightweight, breathable, waterproof and structurally stable in multiple directions.

SUMMARY OF THE INVENTION

The present invention is directed generally to a customizable fitted device for immobilizing particular portions of a user's body. The device can be used to protect, stabilize, and/or immobilize the targeted body portion. According to one embodiment of the present invention, the device can include a generally enclosed sidewall divided into one or more shell-sections. The shell-section(s) can be joined together and form one or more longitudinal seams within the device sidewall. Each longitudinal seam can extend from the upper and lower terminal ends of the device. In an embodiment where there is only a single shell-section, the device contains sufficient flexibility, at least in a portion of the device, to allow the sidewall to be separated along the longitudinal seam and be removed from the user without damaging or destroying the device. In an embodiment where there are multiple shell-sections, the multiple longitudinal seams enable the device to be separated and removed from the user without damaging or destroying the device, even while the sidewall is substantially rigid.

According to one embodiment, the enclosed sidewall can have a plurality of voids defined through the sidewall. The plurality of voids can define structural ribs in the sidewall that maintain structural rigidity while still permitting several openings within the sidewall. The device can also include primary openings at the upper and lower ends of the sidewall so that the device can be applied to only a portion of the user's body, such as the lower arm or leg with other portions of the user's body protruding from the device. Additionally, the device can include secondary openings defined within the sidewall to accommodate thumbs, finger, or other body portion.

The device can further include one or more connector receivers positioned on the longitudinal seams of the device. The connector receivers can be used to hold the one or more sidewall sections together along the one or more longitudinal seams. Each connector receiver is positioned on both portions of the sidewall adjacent to the longitudinal seam. For example, in an embodiment where there are two sidewall- or shell-sections, each connector receiver is positioned on both sidewall sections adjacent to a longitudinal seam. The connector receiver can further be divided along the longitudinal seam so that one portion of the receiver remains on one side sidewall and the other portion of the receiver remains on the adjacent side of the sidewall when the sidewall is separated along the longitudinal seam. Each connector receiver also can include an opening or slot defined through the receiver. The opening can be configured to allow a connector or clip to be inserted through and hold the two portions of the connector receiver together.

When the device is ready for use, the one or more sidewall sections can be placed around the target area of the user so that the one or more sidewall sections meet at the one or more longitudinal seams, thereby forming an enclosed sidewall around the target area. The connectors or clips can then be inserted through the receiver openings and secured to holder the connector receivers together. Once all connector receivers are secured, the device forms a rigid or supporting device around the target area. The device can then be easily removed from the user by removing the connectors or clips and separating the sidewall section(s).

Other aspects and advantages of the present invention will be apparent from the following detailed description of the preferred embodiments and the accompanying drawing figures Other systems, methods, features and advantages of the disclosure will be, or will become, apparent to one of ordinary skill in the art upon examination of the following figures and detailed description. It is intended that all such additional systems, methods, features and advantages be included within this description and this summary, be within the scope of the disclosure, and be protected by the following claims.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

In the accompanying drawing, which forms a part of the specification and is to be read in conjunction therewith in which like reference numerals are used to indicate like or similar parts in the various views:

FIG. 1 is a front perspective view of a fitted device for immobilizing a lower arm of a user in accordance with one embodiment of the present invention;

FIG. 2 is a side perspective view of the fitted device of FIG. 1;

DETAILED DESCRIPTION

Figure 3:
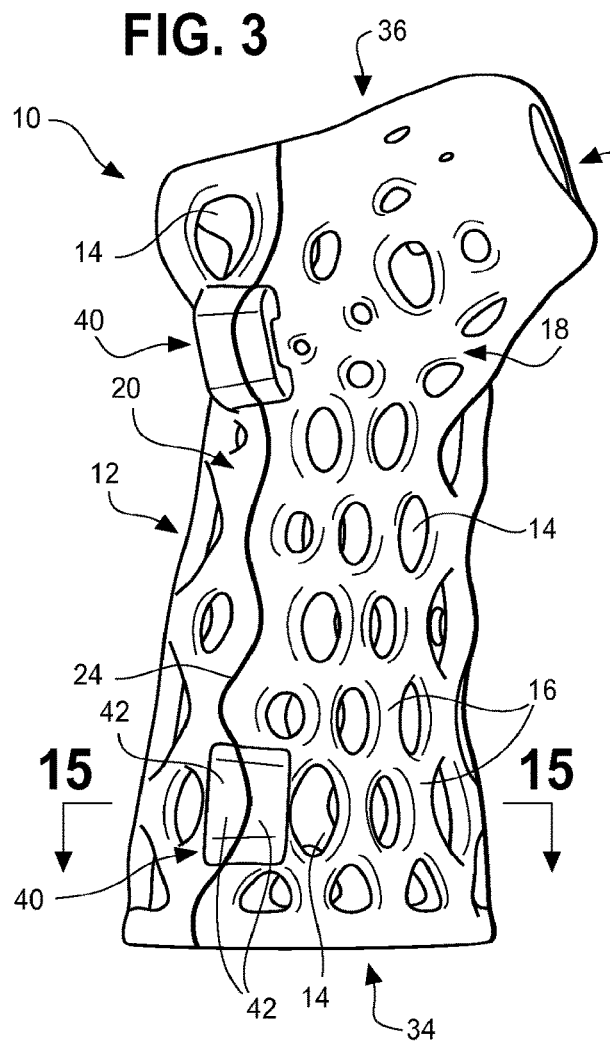
FIG. 3 is a rear perspective view of the fitted device of FIG. 1.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

Figure 7:
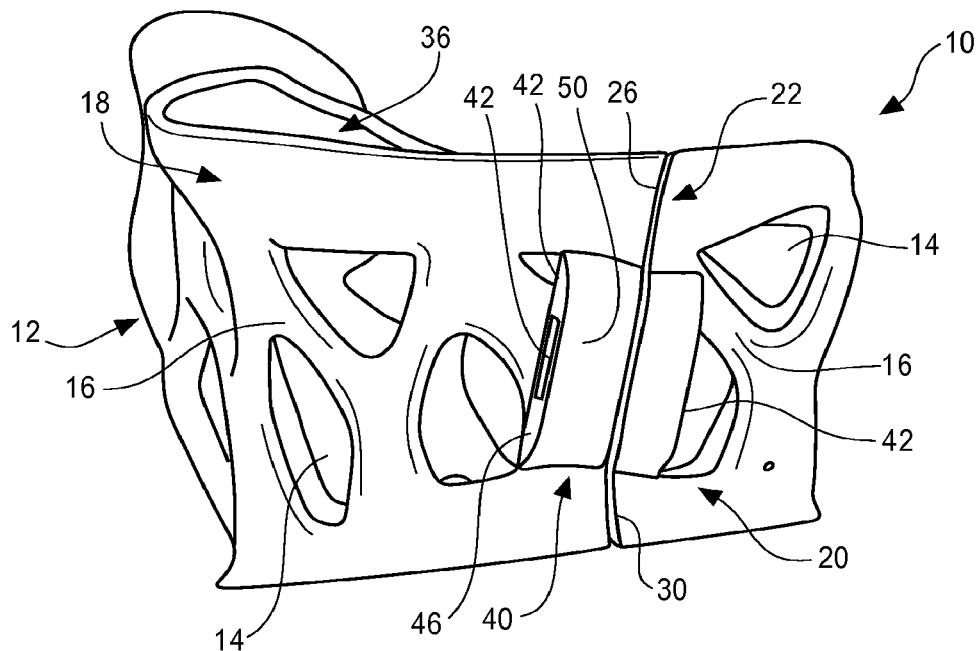
FIG. 7 is a front perspective view of a fitted device for immobilizing a hand of a user in accordance with one embodiment of the present invention.

The present invention is directed toward a fitted device 10. FIG. 1 illustrates one embodiment of the present invention, where device 10 is configured for application to a user's arm. FIG. 7 illustrates another embodiment of the present invention where device 10 is configured for application to a user's hand. As illustrated in the various figures, device 10 can be configured for application to an arm or hand of a human user; however, device 10 can also be suitable for application to other limbs or body parts, such as a leg or foot. Additionally, device 10 as described herein may be used for animals of all types and sizes.

Device 10 can be used to support, stabilize and/or immobilize a limb or similar target area of a user by forming a partially enclosed structure around the target area. Device 10 can be formed as a substantially rigid structure without noticeable flexibility or device 10 can be formed with semi-flexible properties in all or some of device 10 depending on the particular intended application of device 10. Device 10 can also substantially conform to the shape and contours of the target area by forming device 10 in accordance with a method of construction as described in greater detail below. As also described below, device 10 can be comprised of one or more sections that can enable device 10 to be easily applied, removed and re-applied to a user without damage to device 10.

As shown throughout the various figures, device 10 can comprise a generally enclosed sidewall 12 having a plurality of voids 14 defined therein. Voids 14 can have any number of different sizes and shapes and can be configured into particular patterns or non-uniformly entangled formations across sidewall 12. As shown in FIG. 1, and in accordance with one embodiment of the present invention, voids 14 can be positioned in a certain configuration within sidewall 12 so as to form a plurality of structural ribs 16 between voids 14. This configuration of voids 14 and ribs 16 can reduce the amount of material necessary to form device 10 and maintain rigidity of device 10 while providing the device with lightweight properties and enabling ventilation and breathability of device 10 with regard to the user's limb or other target area where device 10 is applied while conforming to manufacturing requirements.

Figure 5:
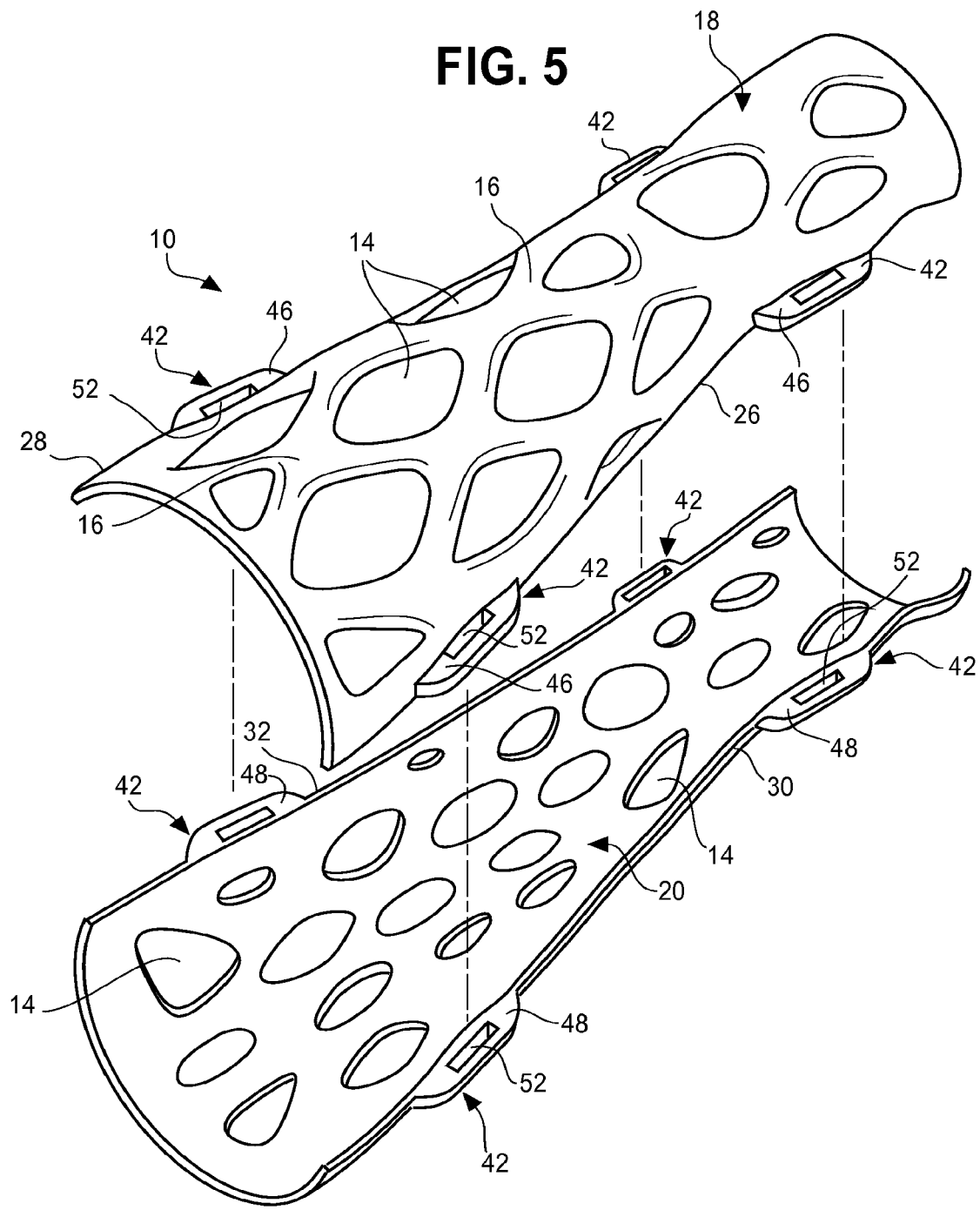
FIG. 5 is an exploded perspective view of the fitted device of FIG. 1, illustrating a first section and a second section of the fitted device separated prior to being applied to a user's arm in accordance with one embodiment of the present invention.
Figure 11:
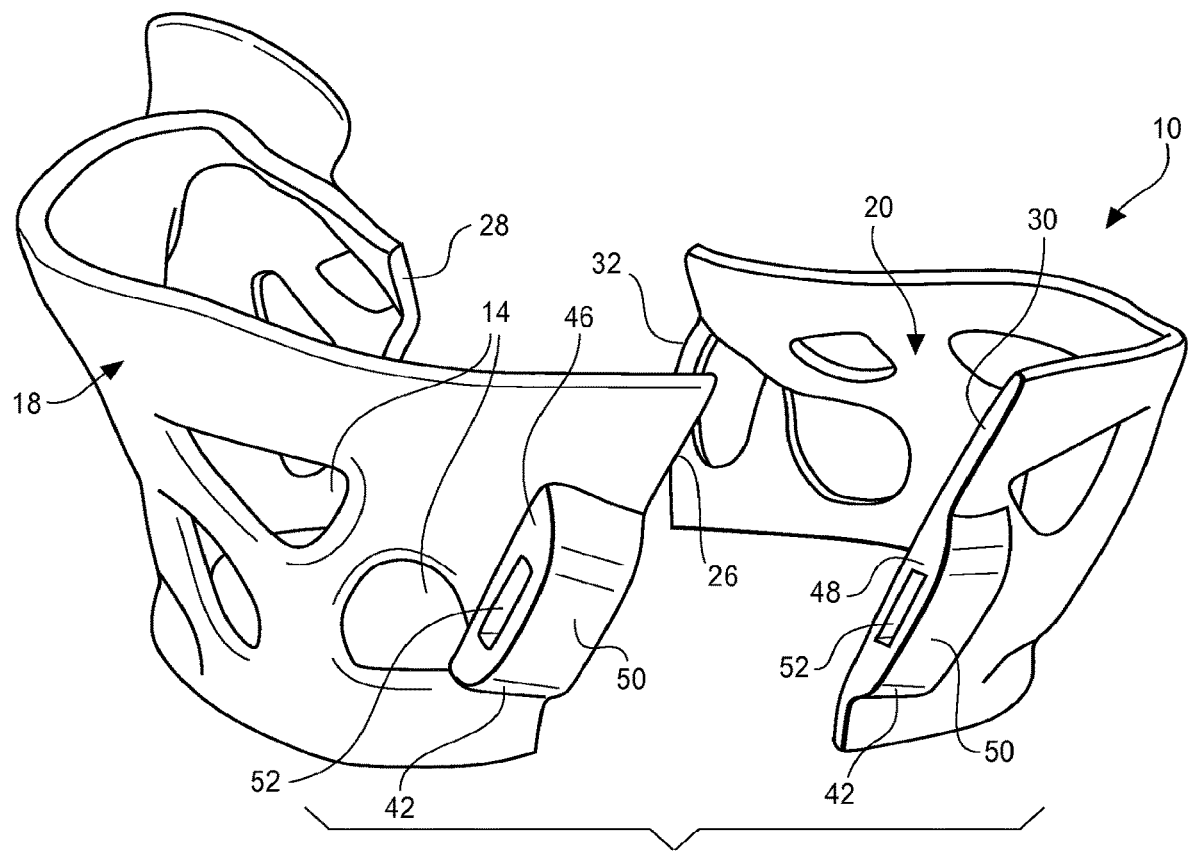
FIG. 11 is an exploded perspective view of the fitted device of FIG. 7, illustrating a first section and a second section of the fitted device separated prior to being applied to a user's hand in accordance with one embodiment of the present invention.
Figure 12:
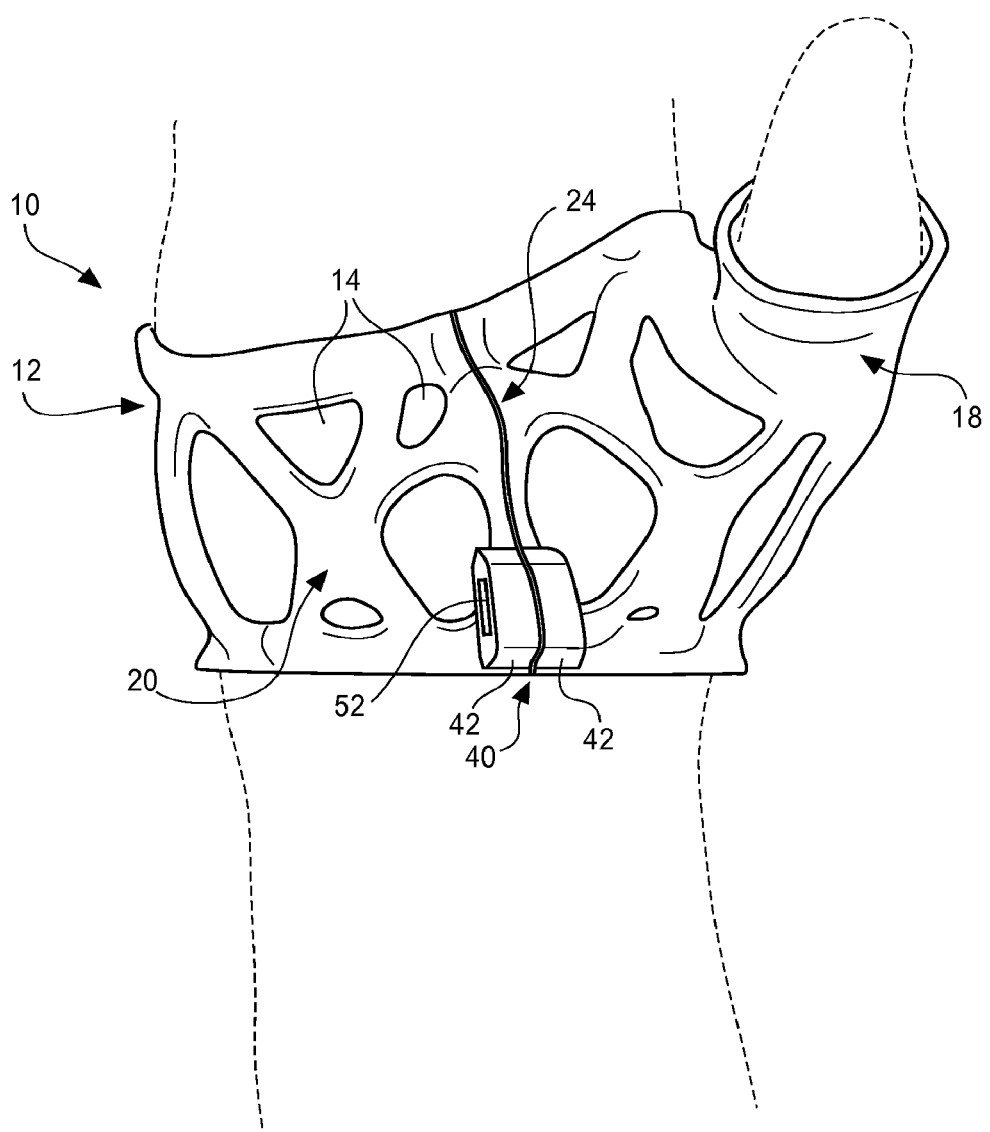
FIG. 12 is a rear perspective view of the fitted device of FIG. 7, illustrating the fitted device applied to a user's hand in accordance with one embodiment of the present invention.
Figure 16:
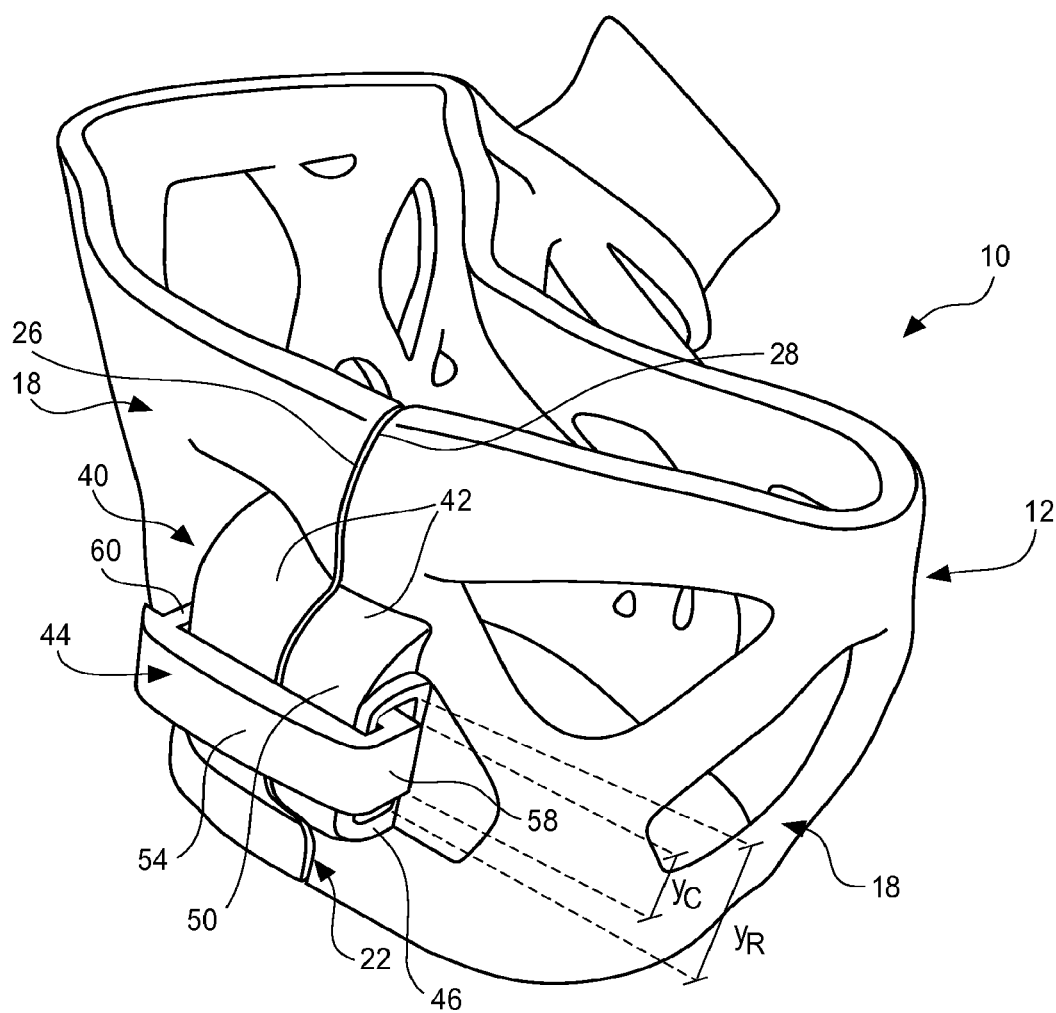
FIG. 16 is a perspective view of a connector and fitted device fitted device for immobilizing a user's hand in accordance with one embodiment of the present invention, illustrating the connector inserted into a receiver slot and holding two end of the fitted device together.

Device 10 can further comprise one or more shell-sections 18, which can be joined together to form the enclosed sidewall 12. As shown in FIG. 16, device 10 comprises a shell-section 18, which can be joined at its ends 26 and 28 to form the enclosed sidewall 12. As shown in FIGS. 5 and 11, device 10 can comprise a shell-section 18 and a shell-section 20, which can be joined together to form the enclosed sidewall 12. Device 10 can also comprise more than two sidewall sections in alternative embodiments of the present invention (this alternative embodiment is not shown in the figures).

In an embodiment where device 10 includes one shell-section 18, sidewall 12 can include a sidewall seam 22 defined longitudinally through sidewall 12. Sidewall seam 22 can define a first and a second longitudinal ends 26 and 28 of shell-section 18, which join together to form sidewall seam 22. Sidewall seam 22 can be configured in a general wave-like configuration or a generally straight configuration. Alternative configurations can also be used, especially configurations that further the structural stability of the device 10. A wave-like configuration can also be configured to provide structural stability of the device 10.

As best illustrated in FIGS. 1 and 3, in an embodiment where device 10 includes shell-sections 18 and 20, shell-sections 18 and 20 can be defined by sidewall seams 22 and 24 defined longitudinally through sidewall 12 and thereby separating sidewall 12 into shell-sections 18 and 20. As shown in FIGS. 1 and 3, when both shell-sections 18 and 20 form sidewall 12, shell-section 18 has first and second longitudinal edges 26 and 28 that correspond to first and second longitudinal edges 30 and 32 of shell-section 20. Longitudinal edges 26 and 30 combine to form first seam 22 while longitudinal edges 28 and 32 combine to form second seam 24. As shown in FIG. 3, seams 22 and 24 (along with corresponding longitudinal ridges 26-32) can be configured in a general wave-like pattern, as shown in FIG. 3, or can have a straighter configuration as shown in FIG. 7. Other configurations or orientations can also be used for seams 22 and 24 so long as seams 22 and 24 are suitable for joining shell-sections 18 and 20 together. Seams 22 and 24 can be formed (and correspondingly, enclosed sidewall 12) when first longitudinal edge 26 of shell-section 18 is joined to conforming first longitudinal edge 30 of shell-section 20 and second longitudinal edge 28 of shell-section 18 is joined to conforming second longitudinal edge 32 of shell-section 20. When shell-sections 18 and 20 are joined together at seams 22 and 24 to form enclosed sidewall 12, adjacent longitudinal edges 26 and 30 and 28 and 32 can be positioned with minimal space defined between.

Figure 4:
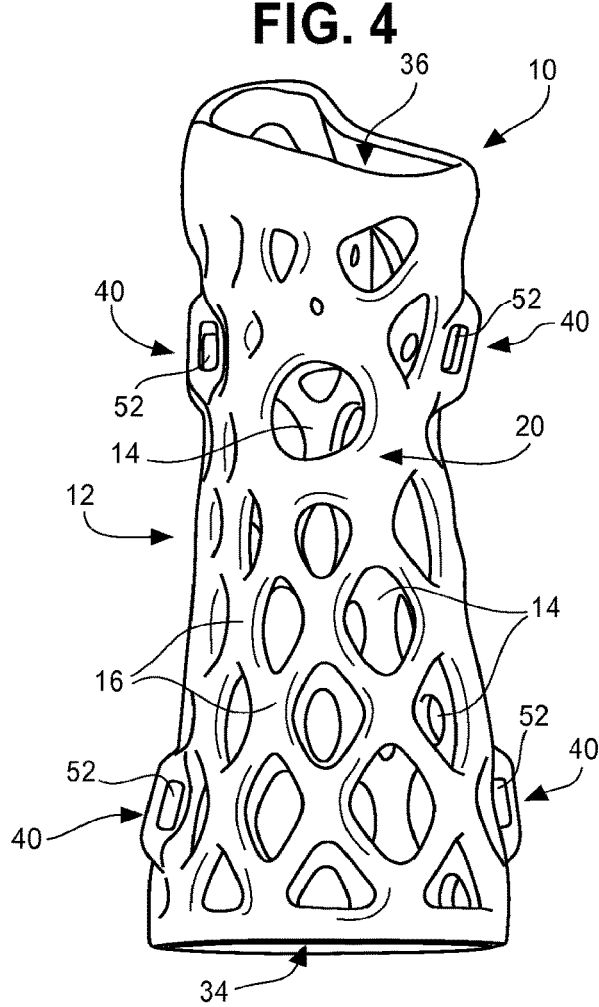
FIG. 4 is a side perspective view of the fitted device of FIG. 1.
Figure 14:
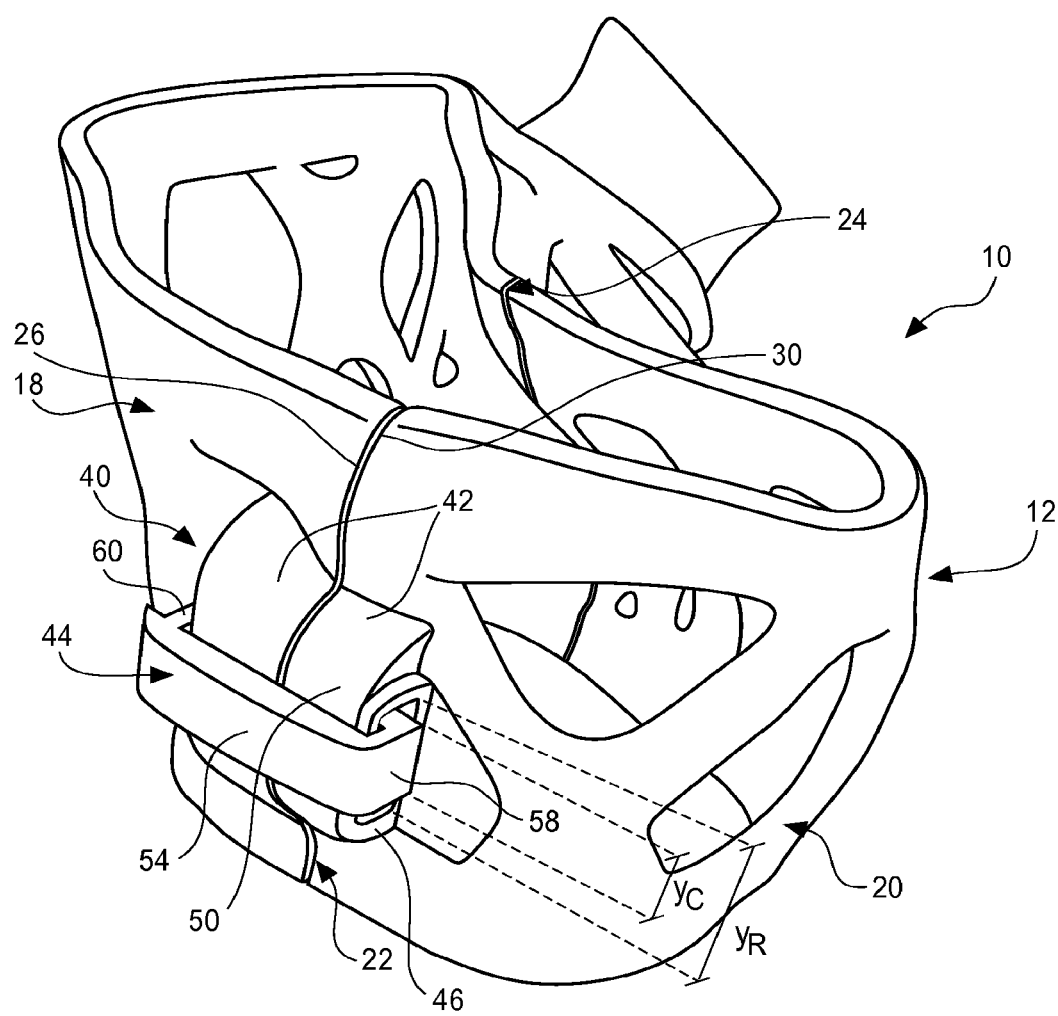
FIG. 14 is a perspective view of a connector and fitted device for immobilizing a user's hand in accordance with one embodiment of the present invention, illustrating the connector inserted into a receiver slot and holding two sections of the fitted device together.

Enclosed sidewall 12 can also define primary end openings 34 and 36 of device 10 at sidewall's 12 terminal or axial ends, as best illustrated in FIGS. 4 and 14. Primary end openings 34 and 36 can accommodate a user's arm, hand, fingers, leg, foot, etc. extending away from device 10 in either direction. Depending on the particular application or use, device 10 can also include secondary openings 38 for thumbs, fingers or similar extremities. As shown in FIG. 2, device 10 can include a secondary opening 38 for receiving a user's thumb, according to one embodiment of the present invention.

Figure 9:
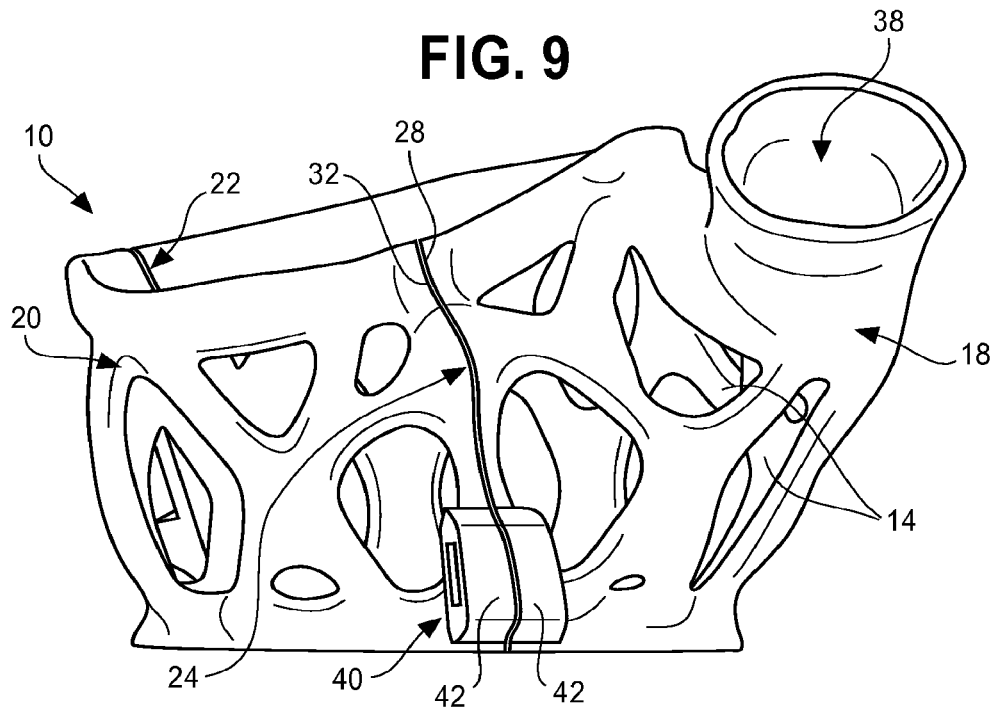
FIG. 9 is a rear perspective view of the fitted device of FIG. 7.
Figure 10:
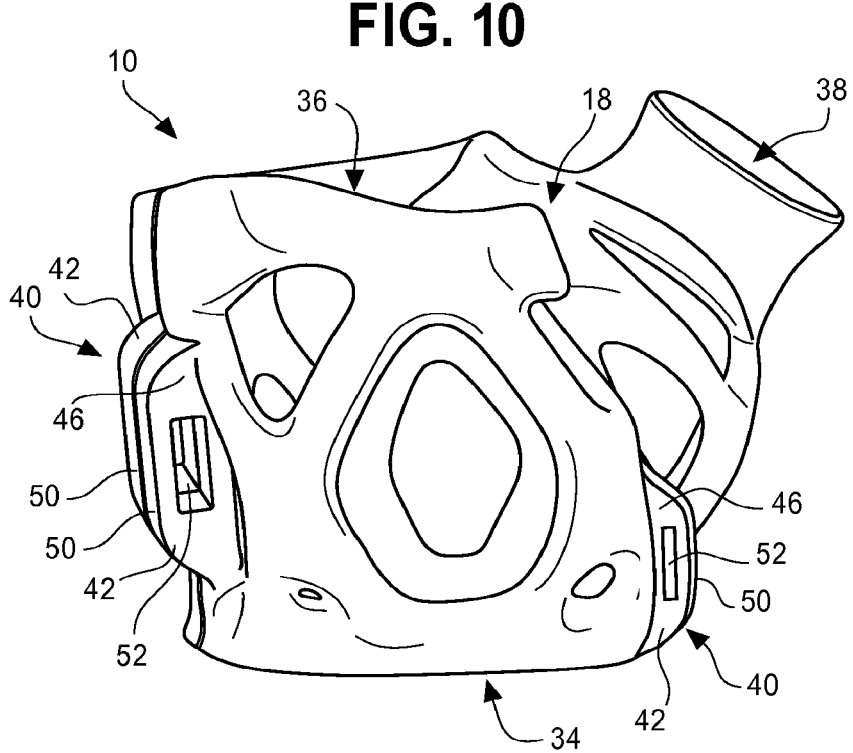
FIG. 10 is a side perspective view of the fitted device of FIG. 7.

Device 10 can also include one or more connector receiver pairs 40 located on seams 22 and/or 24 and comprising two connector receivers 42. As described below, each connector pair 40 can be separable into two portions to allow shell-section 18 to be separated at its ends 26 and 28 or to be separated from shell-section 20. FIG. 2 illustrates one embodiment of device 10 having two receiver pairs 40 along each seam 22 and 24 while FIGS. 9 and 10 illustrate another embodiment of device 10 having only one receiver pair 40 along each seam 22 and 24. FIG. 16 illustrates yet another embodiment of device 10 having only one receiver pair along seam 22, which connects the first and second longitudinal ends 26 and 28 of shell-section 18 together. Any number of additional combinations of receiver pairs 40 may be suitable depending on the particular configuration and shape of device 10. Receiver pairs 40 can be used in conjunction with connectors 44 to secure and hold shell-sections 18 and 20 together along seams 22 and 24, as best shown in FIG. 14, or to secure shell-section 18 together at its ends 26 and 28, as best shown in FIG. 16.

Each connector receiver 42 can extend axially away from sidewall 12 adjacent to seam 22 or 24 (and corresponding longitudinal edge 26-32) as best shown in FIG. 11. As also shown in FIG. 11, each connector receiver 42 can also have first and second raised sidewalls 46 and 48 and a top wall 50 extending therebetween and defining the upper boundary of the receiver 40. Defined within each connector receiver 40 can be a slot 52 extending from first raised sidewall 46 to second raised sidewall 48 for receiving a section of connector 44.

Figure 8:
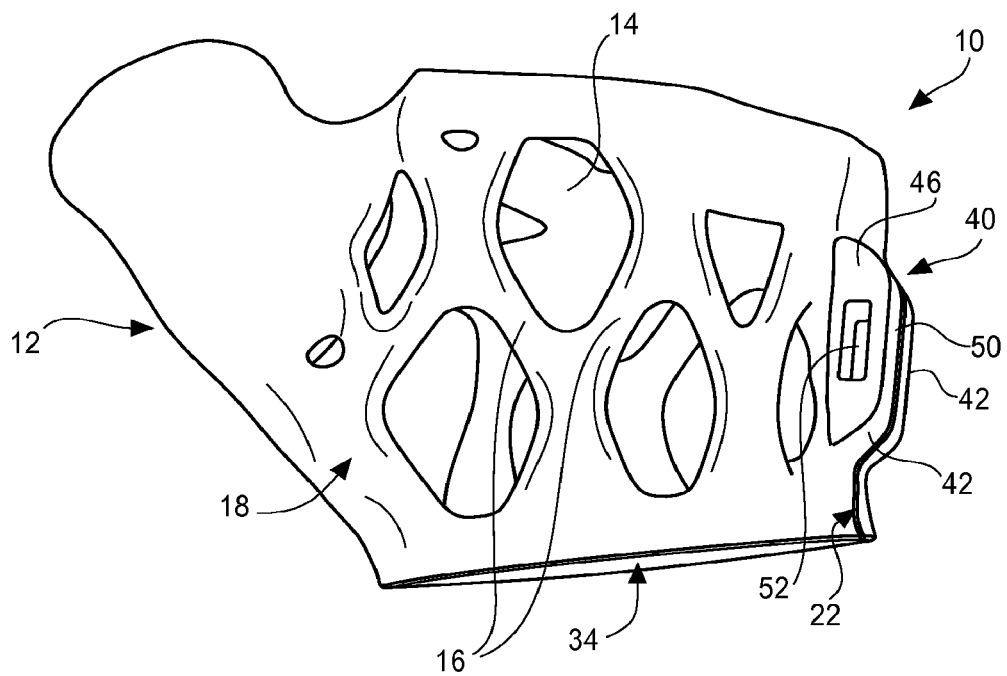
FIG. 8 is a front perspective view of the fitted device of FIG. 7.

As shown in FIG. 11, second raised sidewall 48 of each receiver 42 can conform to the corresponding longitudinal edge 26-32 adjacent to the receiver 42 so that each receiver 42 does not extend beyond seam 22 or 24 and first and second shell-sections 18 and 22 can be joined at seams 22 and 24 with a conforming fit. As best shown in FIGS. 1 and 3, each connector receiver 42 on first longitudinal edge 26 of shell-section 18 corresponds to each connector receptacle 42 on first longitudinal edge 30 of shell-section 20 so that the receivers 42 align along seam 22 and form receiver pairs 40. Similarly, each connector receiver 42 on second longitudinal edge 28 of shell-section 18 can align with each connector receiver 42 on second longitudinal edge 32 of section-shell 18 to form receiver pairs 40. Alternatively, when sidewall 12 comprises only one shell-section 18, as shown in FIG. 16, each connector receiver 42 on first longitudinal edge 26 corresponds to a connector receiver 42 on second longitudinal edge 28 so that the receivers 42 align along seam 22 to form a receiver pair 40. Pursuant to this alignment, slots 52 of corresponding connector receivers 42 in a receiver pair 40 align to form a continuous slot or opening 52 through the receiver pair 40 when shell-sections 18 and 20 are joined together, as best shown in FIG. 8, or when ends 26 and 28 of shell-section 18 are joined together, as best shown in FIG. 16.

Figure 13:
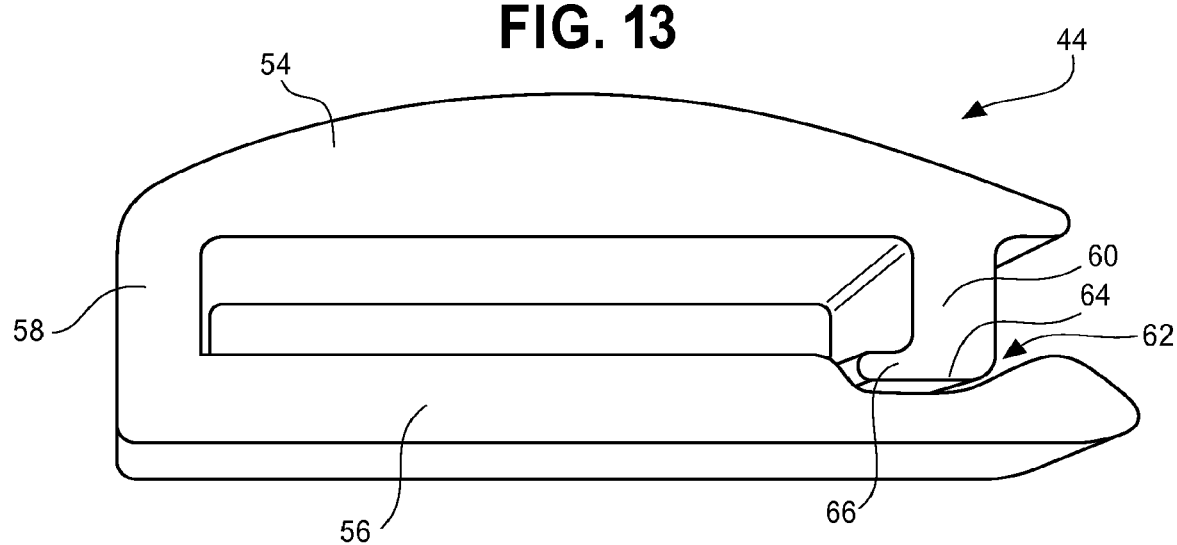
FIG. 13 is a top perspective view of a connector used to secure two sections of a fitted device in accordance with one embodiment of the present invention.

Connectors 44 can be used to lock receivers 42 in each connector receiver pair 40 together to join shell-section 18 at its ends as shown in FIG. 16, or to join shell-section 18 and 20 together as shown in FIG. 14. Connectors 44 can comprise many different types of fasteners depending on the particular embodiment of the present invention. FIG. 13 illustrates one specific embodiment of connector 44 in the form of a clip. As shown in FIG. 13, clip 44 can comprise an upper arm 54 and a lower arm 56 connected together by a resilient bridge 58 at one end of each arm. At its end opposing bridge 58, clip 44 can include a retaining rib 60 extending downward from upper arm 54 into a groove 62 defined in lower arm 56. Retaining rib 60 can include a lower edge 64 that has an inward-extending lip 66 as best shown in FIG. 13. Lip 16 facilitates securing connector pairs 42 together as described in greater detail below. Resilient bridge 58 allows upper arm 54 (and attached rib 60) to be flexed upward away from lower arm 56 by a user to fasten clip 44 to receptacle pair 40, as also described in greater detail below.

Figure 15:
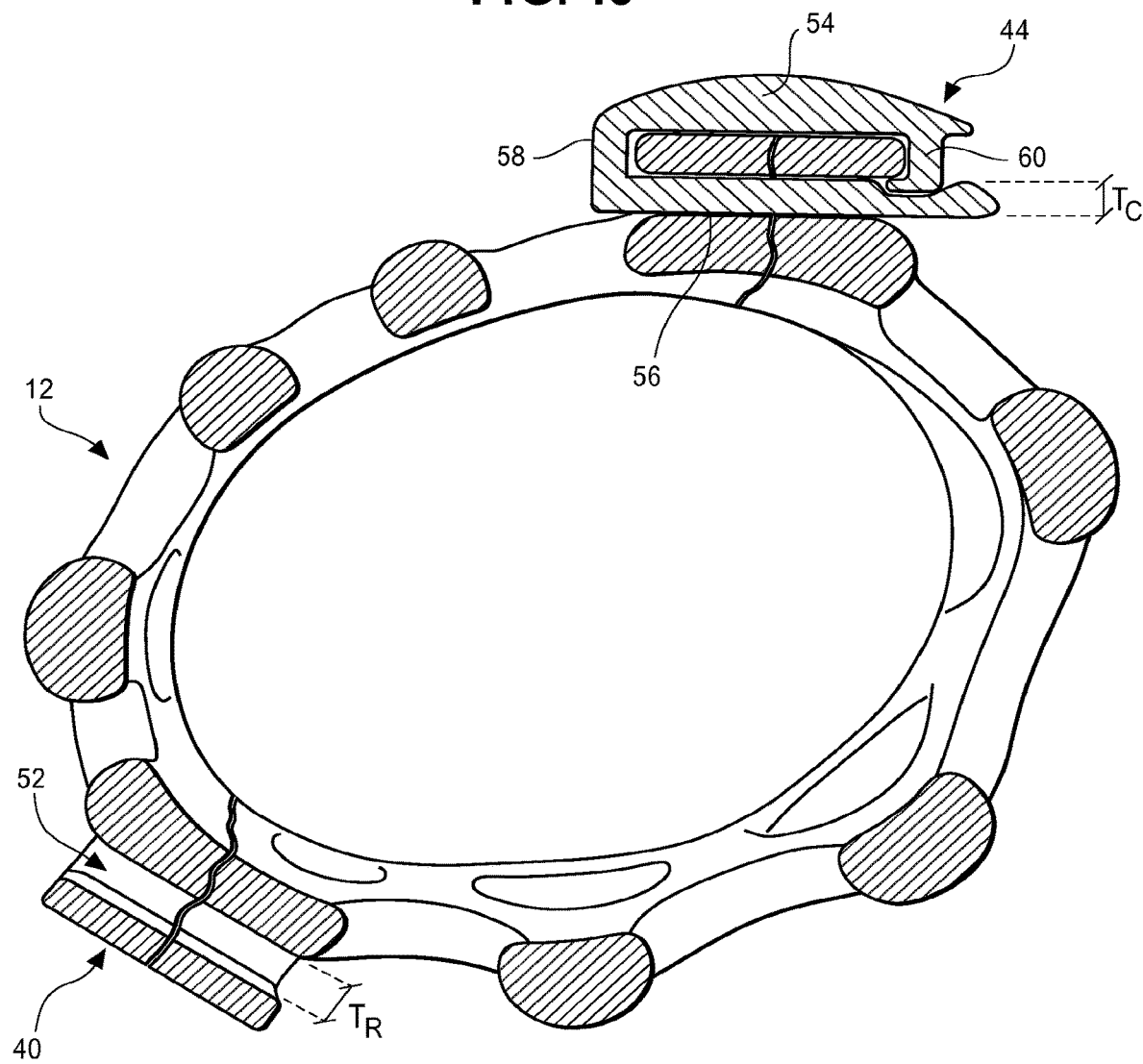
FIG. 15 is a section plan view of the fitted device of FIG. 3, illustrating a connector inserted into a receiver slot for holding a first section and a second section of the fitted device together.

Lower arm 56 can be configured to be inserted into and through receiver slots 52 of a connector receiver pair 40 when joined together. According to this configuration, lower arm 56 preferably has a thickness Tc that is less than a height Tr of receiver slot 52 of receiver pair 40 as best shown in FIG. 15. Lower am1 56 also preferably has a width Yc that is less than a width Yr of receiver slot 52 as best shown in FIG. 14. As shown in FIG. 15, the distance between resilient bridge 58 and retaining rib 60 is preferably slightly greater than the length of receiver pair 40 so that clip 44 tightly joins receptacles 42 together.

Connectors 46 can also comprise any number of alternative embodiments that are suitable for maintaining a joined connected between first and second shell-halves 18 and 20. In an alternative embodiment (not shown), receiver slots 52 of each receiver pair 40 include a divider wall (not shown) that allows a cord, string, wire or similar tie to semi-permanently secure receivers 42 of each receiver pair 40 together.

Figure 6:
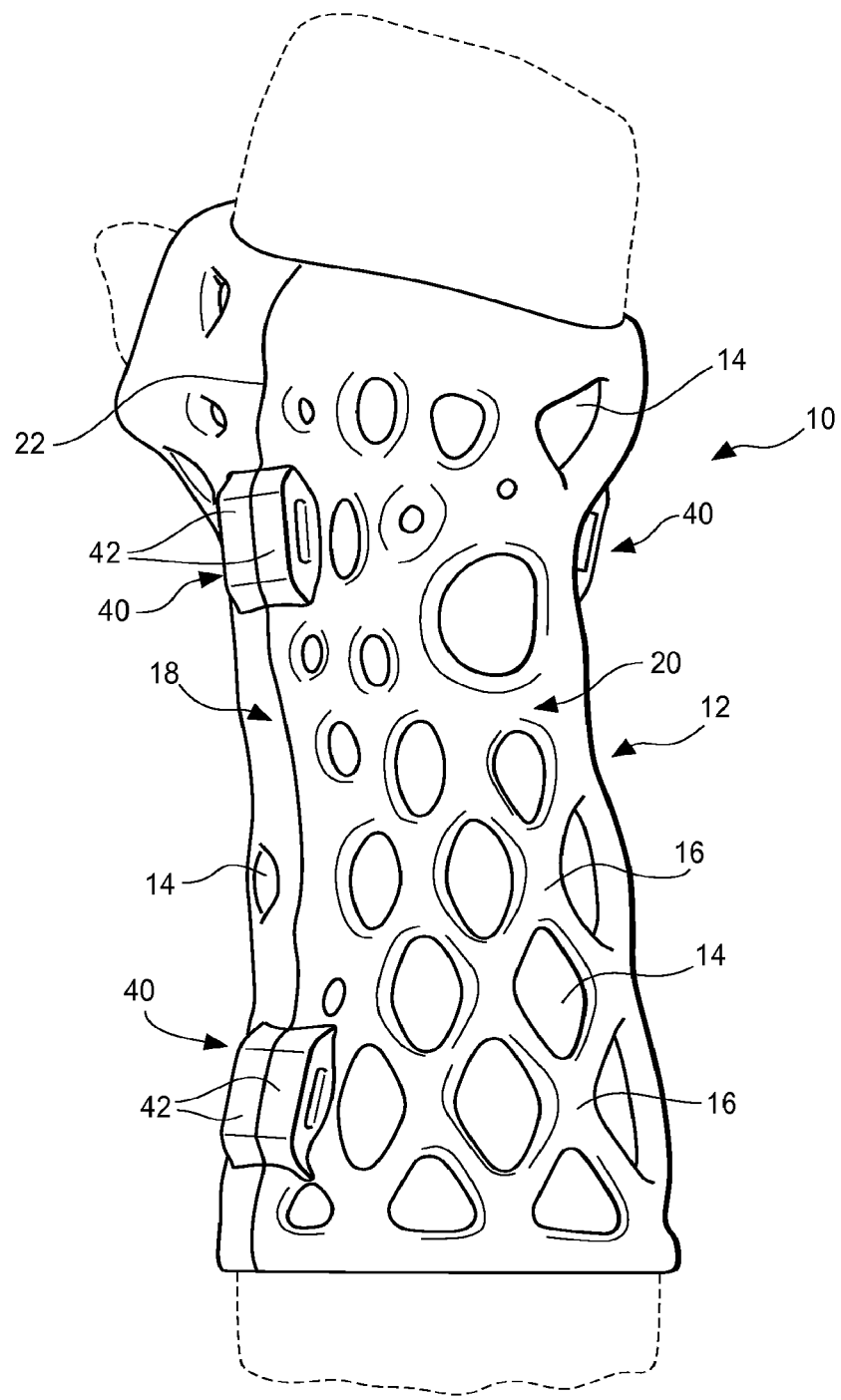
FIG. 6 is a front perspective view of the fitted device of FIG. 1, illustrating the fitted device applied to a user's arm in accordance with one embodiment of the present invention.

As best shown in FIG. 5, prior to use, shell-sections 18 and 20 can be separated from one another. Device 10 can then be used by positioning shell-sections 18 and 20 around the user's target area (such as an arm or leg) and joining first longitudinal edges 26 and 30 to form seam 22 and joining second longitudinal edges 28 and 32 to form seam 24, as best illustrated in FIG. 6. When shell-sections 18 and 20 are joined together along seams 22 and 24, corresponding connector receivers 42 of each receiver pair 40 can be joined together. In an embodiment where sidewall 12 comprises only shell-section 18, the longitudinal ends 26 and 28 can be separated along seam 22 until device 10 can be applied to the target area of the user, where longitudinal seams 26 and 28 can be joined back together.

Connectors 44 can then be used to lock or secure shell-sections together as shown in FIGS. 14-16. When a clip 44 is used as shown in FIGS. 14-16, lower arm 56 of each clip 44 can be inserted into receiver slot 52 of the corresponding receiver pair 40 by raising upper arm 54 away from lower arm 56 until the distance between a lower edge 64 of retaining rib 60 and lower arm 56 is greater than the width top wall 50 of receivers 42. Once lower arm 56 of clip 44 is fully inserted through slot 52, retaining rib 60 snaps downward partially into groove 62 to lock clip 44 in place due to the resiliency of bridge 58. When fully inserted, clip 44 restricts receivers 42 in a receiver pair 40 from separating because top walls 50 of each receiver 42 enclosed by upper arm 54, lower arm 56, resilient bridge 58 and retaining rib 60 of clip 44. Lip 66 on retaining rib 64 can also be positioned partially within slot 52 and thereby prevent upper am1 54 and lower arm 56 from separating. After all clips 44 are inserted into each receiver pair 40 and enclosed around top walls 50, device 10 can be rigidly secured and sidewall 12 can form around the user's arm or other target area.

Device 10 can then be removed from the user by removing connectors 44 and separating first and second shell sections 18 and 20. Because lip 66 can be partially inserted into slot 52, a user can be required to push the resilient bridge laterally against the first sidewall 36 of connector receiver 42 in order to allow lip 66 to exit slot 52. Connectors 44 can then be removed by lifting upper arm 56 away from lower arm 58 and sliding lower arm 58 out of slot 52. Once all connectors 44 are removed from receiver pairs 40, shell-sections 18 and 20 can be removed from the user. Alternatively, when sidewall 12 includes one shell-section 18, longitudinal ends 26 and 28 can be separated in or to allow the device 10 to be removed from the user. Device 10 can then be reapplied in the manner described above.

Collectively, connectors 44 and receiver pairs 40 provide structural stability for the device 10. Each connector 44 can securely hold the connector receivers 44 within a connector receiver pair 40 together and restrict movement along several different directional axes. The sizing of the upper arm 54 and lower arm 56 thicknesses in relation to the top wall 50 thicknesses of the connector receivers 42 restricts movement of one longitudinal end 26-32 relative to another longitudinal end 26-32 along sidewall seam 22 or 24 in a first direction. Lip 66 on retaining rib 64 also assists in preventing this direction of movement by preventing upper and lower arms 54 and 56 from separating unless lip 66 is removed from slot 52. The length of clip 44 between resilient bridge 58 and retaining rib 60 relative to the length of a connector receiver pair 40 restricts movement of a paired longitudinal ends 26-32 relative to one another along seam 22 or 24 in a second direction. Resilient bridge 58 and retaining rib 60 also restrict movement of paired longitudinal ends 26-32 relative to one another along seam 22 or 24 in a third direction. As a result, device 10 can maintain structural rigidity about sidewall 12 when connectors 44 are secured onto clip receiver pairs 40.

Device 10 can be sized, constructed, and designed according to a number of different methods or processes. According to one process, different information can be collected about the intended user of the device. Such information can be collected by various types of equipment, such as scanners and other similar devices. Some or all of this information can also be collected manually. The collected information can then be used to design device 10 according to specific parameters. The information can be used in conjunction with one or more computer analysis programs or software, and other technology in order to develop the design of device 10. The information can also be in a human design process to develop device 10.

The design of device 10 can take into account several different parameters. For example, the design can be dependent on the user, the intended application of device 10, desired immobilization, desired stability, size, shape, temperature, conditions, etc., each of which can affect the material used, the type of scanning device or printer used, and the like. According to one process, the information collected is used to design a device 10 specifically customized to a user with lightweight, breathable, waterproof, and structural stability properties. Further, the process can incorporate additional factors, such as the degree of removability, degree of immobilization of the target area, among others. Based on the foregoing, the design process, according to one embodiment of the present invention, can collect different information specific to a user, combine the collected information with additional design information non-specific to the user, combine, manipulate, and factor the collected and additional information using computer implemented devices, a human design process or a combination of the two in order to develop the design of device 10 specifically adapted to the user in structure and functionality.

According to one method, device 10 can be formed using a 3D scanner to precisely identify the shape and contours of the user's target area. The 3D scanner can incorporate a hand-held, white-light reflective scanner that can be selectively positioned around the user's arm or other body part in which device 10 will be applied to create a 3D image of the target area. Additional information can be collected and incorporated in certain applications. 3D CAD software, along with other design software, can then be used to design the device 10 to precisely fit around 3D image by effectively drawing the shape of the device 10 onto the 3D image model. Voids 14 and corresponding structural ribs 16 can then be selectively designed into device 10. Seams 22 and/or 24 can then be provided onto the design of device 10 to form shell-section 18 and shell-section 20, if applicable. Connector receiver pairs 40 can then be provided onto device 10 along seams 22 and/or 24. Connectors 44 can also be designed to correspond to receiver pairs 40. Device 10 can then be constructed by printing each shell-section 18 and 20

(if applicable) using a 3D printer. Device 10 can be constructed from several different materials depending on the particular application of device 10. Device 10 can be constructed from a uniform material or a combination of materials. The specific material used can affect the flexibility, rigidity, structural stability, weight and other properties of the device. In one embodiment, device 10 is constructed from a rigid material such as rigid plastic. In an alternative embodiment, device 10 is constructed from a semi-rigid or semi-flexible material, such as flexible plastic or woven fabric material.

From the foregoing, it will be seen that this invention is one well adapted to attain all the ends and objects hereinabove set forth together with other advantages which are inherent to the structure. It will be understood that certain features and subcombinations are of utility and may be employed without reference to other features and subcombinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

I claim:

1. A customized removable fitted immobilization device for a body portion comprising:
    a sidewall formed by a first shell section and a second shell section, each of the first and the second shell sections having a first longitudinal edge and a second longitudinal edge, wherein the first longitudinal edge and the second longitudinal edge of each shell section collectively forms a plurality of longitudinal edges, and wherein the sidewall is configured to conform to a shape and one or more contours of the body portion of a specific user as manufactured and prior to being applied to the body portion of the specific user;
    at least one longitudinal sidewall seam extending longitudinally along the sidewall between an upper sidewall edge and a lower sidewall edge, wherein each longitudinal sidewall seam removably joins two longitudinal edges of the plurality of longitudinal edges such that the two longitudinal edges making up the longitudinal side wall seam are directly contiguous to each other along a full length of each longitudinal edge from a first end of the device to a second end of the device;
    wherein the first longitudinal edge and the second longitudinal edge on each of the first shell section and the second shell section extend perpendicular to an outer surface of the sidewall;
    wherein the plurality of longitudinal edges of the first shell section are configured so as to conform to the plurality of longitudinal edges of the second shell section so as to join the first shell section to the second shell section;
    a first connector receiver pair positioned along a first at least one longitudinal sidewall seam, the first connector receiver pair comprising:
        a first connector receiver positioned on the sidewall and adjacent to the first at least one longitudinal sidewall seam, the first connector receiver having a slot defined therein; and
        a second connector receiver positioned on the sidewall and adjacent to the first at least one longitudinal sidewall seam and positioned opposing the first connector receiver relative to the first at least one longitudinal sidewall seam, the second connector receiver having a slot defined therein; and
    a first connector configured for securing the first and second connector receivers of the first connector pair together when the sidewall is joined along the first at least one longitudinal sidewall seam;
    wherein, when the first connector secures the first and second connector receivers, the first connector receiver pair and the first connector together provide structural stability for the device in three directional axes;
    wherein the sidewall is substantially rigid without noticeable flexibility.

2. The device of claim 1, wherein the first at least one longitudinal sidewall seam has a configuration such that the two longitudinal edges making up the longitudinal sidewall seam conform to one another other, such that the longitudinal sidewall seam provides structural stability to the device.

3. The device of claim 1, wherein the first at least one longitudinal sidewall seam has a wave-like configuration.

4. The device of claim 1, wherein the first shell and the second shell are configured such that the device can be easily applied, removed, and re-applied to the body portion of the specific user without damage to the device.

5. The device of claim 1, wherein the device is constructed by printing each of the first shell and the second shell using a 3D printer.

6. The device of claim 5, wherein the sidewall has a plurality of voids defined in the sidewall, and a configuration of the plurality of voids defines a plurality of structural ribs, each structural rib located between two or more voids of the plurality of voids.

7. The device of claim 6, wherein the plurality of voids is arranged in a configuration that provides structural stability for the device.

8. The device of claim 1, wherein the first connector receiver is positioned adjacent to the second connector receiver so that the slots of the first and the second connector receivers align to form a continuous opening of the connector receiver pair when the sidewall is joined together at the first at least one longitudinal sidewall seam.

9. The device of claim 8, wherein the first and second connector receivers each contain a receiver wall located along the first at least one longitudinal sidewall seam, and wherein the receiver walls have a configuration relative to one another that provides structural stability for the device along the first at least one longitudinal sidewall.

10. The device of claim 1, wherein each connector receiver further comprises:
   a top wall extending away from the device sidewall in a generally perpendicular direction;
   a first receiver wall positioned laterally inward from the first at least one longitudinal sidewall seam and extending generally perpendicular between the device sidewall and the receiver top wall; and
   a second receiver wall positioned along the first sidewall seam and extending between the device sidewall and the receiver top wall, the second receiver wall generally conforming to the first at least one longitudinal sidewall seam;
   wherein the receiver slot is defined between the first and the second receiver walls and extends generally perpendicularly from the first and the second lateral walls.

11. The device of claim 10, wherein the second receiver wall of the first connector receiver conforms to the second receiver wall of the second connector receiver.

12. The device of claim 1, wherein the connector comprises a configuration that structurally stabilizes the device in the three directional axes when the connector is securing the first connector receiver pair.

13. The device of claim 1, wherein the device includes a primary opening at each of the first end of the device and the second end of the device, and further includes at least one secondary opening.

14. The device of claim 1, wherein
   the at least one longitudinal sidewall seam comprises a first longitudinal sidewall seam and a second longitudinal sidewall seam,
   the first longitudinal sidewall seam removably joins a first longitudinal edge of the first shell section and a first longitudinal edge of the second shell section such that the first longitudinal edge of the first shell section and the first longitudinal edge of the second shell section are adjacent to each other, and
   the second longitudinal sidewall seams removably joins a second longitudinal edge of the first shell section and a second longitudinal edge of the second shell section such that the second longitudinal edge of the first shell section and the second longitudinal edge of the second shell section are adjacent to each other.

15. The device of claim 1, wherein the first connector receiver and the second connector receiver are integrally connected to the sidewall.

16. A customized removable fitted immobilization device for a body portion comprising:
   a first shell section and a second shell section, each of the first shell section and the second shell section having a first longitudinal edge and a second longitudinal edge;
   a sidewall formed by the first shell section and the second shell section, the sidewall being configured to conform to a shape and one or more contours of the body portion of a specific user as manufactured and prior to being applied to the body portion of the specific user;
   a first longitudinal sidewall seam and a second longitudinal sidewall seam; and
   wherein the first longitudinal sidewall seam removably joins the first longitudinal edge of the first shell section and the first longitudinal edge of the second shell section such that the first longitudinal edge of the first shell section and the first longitudinal edge of the second shell section are contiguous to each other along a full length of each longitudinal edge from a first end of the device to a second end of the device;
   wherein the second longitudinal sidewall seam removably joins the second longitudinal edge of the first shell section and the second longitudinal edge of the second shell section such that the second longitudinal edge of the first shell section and the second longitudinal edge of the second shell section are contiguous to each other along a full length of each longitudinal edge from a first end of the device to a second end of the device;
   wherein the first longitudinal edge and the second longitudinal edge on each of the first shell section and the second shell section extend perpendicular to an outer surface of the sidewall;
   wherein the plurality of longitudinal edges of the first shell section are configured so as to conform to the plurality of longitudinal edges of the second shell section so as to join the first shell section to the second shell section; and
   wherein the sidewall is substantially rigid without noticeable flexibility.

17. The device of claim 16, wherein the sidewall has a plurality of voids defined in the sidewall, and a configuration of the plurality of voids defines a plurality of structural ribs, each structural rib located between two or more voids of the plurality of voids;
   and wherein the plurality of voids is arranged in a configuration that provides structural stability for the device.

18. The device of claim 17, wherein the device includes a primary opening at each of the first end of the device and the second end of the device, and further includes at least one secondary opening.

19. A customized removable fitted immobilization device for a body portion comprising:
   a first shell section and a second shell section, each of the first shell section and the second shell section having a first longitudinal edge and a second longitudinal edge;
   a sidewall formed by the first shell section and the second shell section, the sidewall being configured to conform to a shape and one or more contours of the body portion of a specific user as manufactured and prior to being applied to the body portion of the specific user;
   a first longitudinal sidewall seam and a second longitudinal sidewall seam; and
   wherein the first longitudinal sidewall seam removably joins the first longitudinal edge of the first shell section and the first longitudinal edge of the second shell section such that the first longitudinal edge of the first shell section and the first longitudinal edge of the second shell section are contiguous to each other along a full length of each longitudinal edge from a first end of the device to a second end of the device;
   wherein the second longitudinal sidewall seam removably joins the second longitudinal edge of the first shell section and the second longitudinal edge of the second shell section such that the second longitudinal edge of the first shell section and the second longitudinal edge of the second shell section are contiguous to each other along a full length of each longitudinal edge from a first end of the device to a second end of the device; and
   wherein the sidewall is substantially rigid without noticeable flexibility.

20. The device of claim 19, further comprising: a first connector receiver pair positioned along one of the first longitudinal sidewall seam and the second longitudinal sidewall seam, the first connector receiver pair comprising: a first connector receiver positioned on the sidewall and adjacent to the longitudinal sidewall seam, the first connector receiver having a slot defined therein; and a second connector receiver positioned on the sidewall and adjacent to the longitudinal sidewall seam and positioned opposing the first connector receiver relative to the longitudinal sidewall seam, the second connector receiver having a slot defined therein.

* * * * *